United States Patent [19]
Aiello et al.

[11] Patent Number: 6,114,320
[45] Date of Patent: Sep. 5, 2000

[54] THERAPEUTIC TREATMENT FOR VEGF RELATED OCULAR DISEASES

[75] Inventors: Lloyd P. Aiello, Belmont, Mass.; Michael R. Jirousek, Indianapolis, Ind.; George L. King, Dover, Mass.; Louis Vignati; Douglas Kirk Ways, both of Indianapolis, Ind.

[73] Assignees: Eli Lilly and Company, Indianapolis, Ind.; Joslin Diabetes Center, Boston, Mass.

[21] Appl. No.: 08/841,739

[22] Filed: Apr. 30, 1997

Related U.S. Application Data

[60] Provisional application No. 60/016,658, May 1, 1996.

[51] Int. Cl.$^7$ ........................ A61K 31/33; A61K 31/555
[52] U.S. Cl. ............................. 514/185; 514/183
[58] Field of Search ...................... 514/183, 185

[56] References Cited

U.S. PATENT DOCUMENTS

| | | |
|---|---|---|
| 5,057,614 | 10/1991 | Davis et al. |
| 5,481,003 | 1/1996 | Gillig et al. |
| 5,491,242 | 2/1996 | Gillig et al. |
| 5,545,636 | 8/1996 | Heath, Jr. et al. |
| 5,552,396 | 9/1996 | Heath et al. |
| 5,621,098 | 4/1997 | Heath, Jr. et al. |

FOREIGN PATENT DOCUMENTS 0 657 411 A1  2/1994  European Pat. Off.

OTHER PUBLICATIONS

Kunisaki et al. "Vitamin E prevents diabetes–induced abnormal retinal blood flow via the diacylglycerolprotein kinase C pathway", Am. J. Physiol. vol. 269, No. 2, 1995 pp. E239–E246.
Aiello, et al., *New England Jour. Medicine*, 331(22):1480–1487 (1994).
Amin, et al., *Invest Ophthalmol Vis Sci.*, 35:3178–3188 (1994).
*Biotechnology Newswatch*, Jan. 1, 1996.
Bird, *Surv. Ophthalmol.*, 28:433–6 (1984).
Bundgaard, H., *Design of Prodrugs*, (1985).
Chan et al., *Ophthalmology*, 101:289–300 (1994).
Cunha–Vaz, *Surv Ophthalmol.* 28:485–92 (1984).
Freund et al., *Amer. Jour. Ophthalmol.*, 115:786–791 (1993).
Friedman, et al., *Amer. J. Kidney Dis.*, 26(1):202–208 (1995).
Henkind, *Surv. Ophthalmol.* 28:431–2 (1984).
Jampol, et al., *Surv. Ophthalmol.* 28:535–9 (1984).
Kirkpatrick et al., *Br. J. Ophthalmol.*, 77:766–770 (1993).
Klein, et al., "Prevalence of Age Related Maculopathy: The Beaver Dam Study," *Ophthalmology*, 99(6):933–943, 1992).
Klein, *Med. Clin. N. Am.*, 72:1415–1437 (1988).
Liebowitz HM, Krueer DE, Maunder LE, et al., "The Framingham Eye Study: VI Macular Degeneration," *Surv. Opthalmol.* 24 (supp 10:428–457, 1980).
Miwa, *Drug Intell. Clin. Pharm.*, 20:548–550 (1986).
MPS Group, *Arch Ophthalmol.*, vol. 109, pp. 1232–1241 (1991).
Raskin, et al., *Ann. Int. Med.*, 117(3):226–233 (1992).
"Researchers Focus on Macular Degeneration: Common Eye Problems, Causes and Treatment Get New Attention" by Steven Sternberg, Washington Post Health, Oct. 31, 1995.
Yannuzzi, *Surv Ophthalmol.* 28:540–53 (1984).
Yannuzzi, et al., *Opthalmology*, 88:947–54 (1981).
Van Effenterre, et al., *J. Francais D Ophtalmol.*, 16(11):602–610 (1993).
Peer B. Jacobson et al. "Anti–inflammatory Properties of Gö 6820: A Selective Inhibitor of Protein Kinase C" Journal of Pharmacology and Experimental Therapeutics, Vo. 275, No. 2 1995 pp. 995–1002.

*Primary Examiner*—Zohreh Fay
*Attorney, Agent, or Firm*—Paul R. Darkes; Steven P. Caltrider

[57] ABSTRACT

A method for inhibiting VEGF stimulated endothelial cell growth, such as associated with macular degeneration, and VEGF stimulated capillary permeability, such as associated with macular edema are disclosed, particularly using the isozyme selective PKC inhibitor, (S)-3,4-[N,N'-1,1'-((2"-ethoxy)-3'"(O)-4'"-(N,N-dimethylamino)-butane)-bis-(3,3'-indoly 1)]-1(H)-pyrrole-2,5-dionehydrochloridesalt.

12 Claims, 10 Drawing Sheets

THERAPEUTIC TREATMENT FOR VEGF RELATED OCULAR DISEASES

This application claims the priority benefits of the U.S. provisional application Ser. No. 60/016,658 filed May 1, 1996.

BACKGROUND OF THE INVENTION

1. Field of the Invention

The present invention is broadly directed to a method for inhibiting endothelial cell growth and capillary permeability associated with vascular endothelial growth factor (VEGF), e.g., the increased cell growth and permeability induced by VEGF using an inhibitor of the β isozyme of Protein Kinase C (PKC). These VEGF induced conditions are closely associated with a variety of ocular vascular disorders.

The present invention is particularly directed to the use of an inhibitor of the β isozyme of Protein Kinase C (PKC) for treating ocular vascular disorders including macular degeneration, macular edema, vascular retinopathy, retinal vein occlusion, iris neovascularization, histoplasmosis, and ischemic retinal diseases.

2. Description of Related Art

VPF/VEGF is a glycosylated, multifunctional cytokine. Over-expression of VPF/VEGF is associated with a variety of ocular vascular disorders.

VPF/VEGF induces endothelial cell proliferation, excessive permeability via activation of vesicular-vacuolar organelle mediated transport, migration and actin reorganization with shape changes and ruffling. It alters endothelial cell gene expression, inducing increased production of tissue factor and several proteases, including interstitial collagenase and both the urokinase-like and tissue plasminogen activators. The majority of these same genes are induced by phorbol myristate acetate (PMA) stimulated activation of PKC.

Vascular endothelial growth factor (VEGF) along with both fibroblast growth factors (FGFs) and transforming growth factor (TGFβ) are thought to play a major part in mediating active intraocular neovascularization in patients with ischemic retinal diseases (Aiello, et al., *New England Jour. Medicine,* 331(22):1480–1487 (1994); Amin, et al., *Invest Ophthalmol Vis Sci.,* 35:3178–3188 (1994)).

One of the ocular vascular disorders associated with increased VEGF expression is macular degeneration. Age related macular degeneration is the leading cause of blindness in the elderly. It is estimated that macular degeneration afflicts more than 16% of people 85 and older, and 6% of people between the age of 65 and 74. Greater than 20% of patients over the age of 75 have macular degeneration. The disease is more frequent in women (Liebowitz H M, Krueer D E, Maunder L E, et al., "The Framingham Eye Study: VI Macular Degeneration," *Surv. Opthalmol.* 24 (supp 10:428–457, 1980); Klein, et al., "Prevalence of Age Related Maculopathy: The Beaver Dam Study," *Ophthalmology,* 99(6):933–943, 1992). Macular degeneration can be divided into dry or wet type, the dry type being 10 times more common, but generally less severe in its clinical manifestations. The more severe wet, or exudative macular degeneration, is associated with the abnormal growth of choroidal vessels (choroidal neovascularization) into the subretinal pigment epithelium or subretinal space and often leads to severe visual impairment.

Macular degeneration has the initial pathologic lesion of appearance of drusen which represents abnormal tissue deposition within the retinal pigment epithelial (RPE) layer and is thought to be secondary to vascular insufficiency. New blood vessels then grow through Bruch's membrane which is between the RPE and the choriocapillaries to invade the retina. This retinal invasion causes destruction of the photoreceptors and can lead to hemorrhage which reduces vision.

One of the most common forms of treatment for macular degeneration is laser therapy. Laser therapy is used to treat areas of neovascularization that do not extend into the central macular area (fovea). However, recurrence of the disease is common after laser therapy. (MPS Group, *Arch Ophthalmol.,* Vol. 109, pp. 1232–1241 (1991)) Moreover, laser therapy can result in residual scotomata and therefore is not an optimal treatment of neovascularization in the central macular region. Only a limited number of patients meet eligibility criteria for this form of treatment, principally because of the ill-defined, or occult nature, of the choroidal neovascularization commonly seen. (Freund et al., *Amer. Jour. Ophthalmol.,* 115:786–791 (1993)) Interferon also has been tried as a therapeutic agent based on the known activity of growth factors such as fibroblast growth factor on stimulation of pathologic angiogenesis. However, no consistent effect has been observed. (Kirkpatrick et al., *Br. J. Ophthalmol.,* 77:766–770 (1993); Chan et al., *Ophthalmology,* 101:289–300 (1994)). More recently, a trial using transforming growth factor (TGF) beta-2 for treating macular degeneration was unsuccessfully concluded. *Biotechnology Newswatch,* Jan. 1, 1996.

With rapid aging of the population, macular degeneration poses a substantial public health problem. At present, there is no cure and the less than satisfactory results obtained with laser treatment is the only accepted therapy, though the FDA recently approved thalidomide for use in a clinical study with human patients. ("Researchers Focus on Macular Degeneration: Common Eye Problems, Causes and Treatment Get New Attention" by Steven Sternberg, Washington Post Health, Oct. 31, 1995). There remains a strong need in the art for an effective drug therapy for macular degeneration.

Macular edema is associated with many types of ocular vascular diseases, such as retinitis pigmentosa, diabetic retinopathy, pars planitis, retinal vein obstruction, senile hyalitis, and with intraocular surgical procedures (Henkind, *Surv. Ophthalmol.* 28;431–2 (1984); Bird, *Surv. Ophthalmol.,* 28:433–6 (1984); Cunha-Vaz), *Surv Ophthalmol.* 28:485–92 (1984)). Cystoid macular edema is the most common complication following cataract surgery (Yannuzzi, *Surv Ophthalmol.* 28:540–53 (1984)) and probably the most common cause of visual loss in patients undergoing lens extraction (Jampol, et al., *Surv. Ophthalmol.* 28:535–9 (1984)). Cystoid macular edema is usually self-limited and even chronic cases can spontaneously improve (Yannuzzi, *Surv Ophthalmol.* 28:540–53 (1984)). However, a small proportion of patients (1 to 15%) may develop irreversible damage and permanent visual disability (Yannuzzi, et al., *Opthalmology,* 88:847–54 (1981)).

Macular edema is also a cause of late loss of vision in patients with the Vogt-Koyanagi-Harada (VKH) syndrome (Rutzen, et al., *J. Ret. and Vit. Dis.,* 15(6):475–479 (1995)). Macular edema is closely associated with microaneurysms in diabetic retinopathy and in nondiabetic persons with sickle cell anemia, branch vein occlusion, carotid artery disease, or severe hypertension (Klein, *Med Clin. N. Am.,* 72:1415–1437 (1989)). Microaneurysms often leak lipoprotein material, which results in the formation of hard exudates. These exudates appear in a scattered, aggregated, or ring-like configuration. When exudates and fluid collects in the posterior part of the retina, macular edema can result, which can cause significant blurring of vision and lead to loss of visual acuity.

A laser procedure, called focal photocoagulation, is used to treat the areas of retinal swelling adjacent to microaneurysms. Focal photocoagulation has been shown to decrease the incidence of deterioration of visual acuity by 60% in patients with clinically significant macular edema, but no benefit of photocoagulation has been shown in patients with mild-to-moderate macular edema (Raskin, et al., *Ann. Int. Med,* 117(3):226–233 (1992)). Vitreous surgery can improve the visual prognosis only in cases of diabetic macular edema associated with a pathological vitreo-macular interface (Vaneffenterre, et al., *J. Francais D Ophtalmol.,* 16(11) :602–610 (1993)). Drug treatments such as oral and topical indomethacin (Miwa, *Drug Intell. Clin. Pharm.,* 20:548–550 (1986)), as well as erythropoietin (Friedman, et al., *Amer. J. Kidney Dis.,* 26(1):202–208 (1995)) have been evaluated for macular edema but no significant effect has been observed. There is a need in the art for an effective drug therapy for macular edema.

While VEGF was known to play some role in the pathology of certain ocular vascular disorders, it remained to be determined whether inhibiting the function provided by VEGF would provide a therapeutic benefit to the treatement of such ocular vascular disorders. The present invention demonstrates that by inhibiting the activity of VEGF one can amelorate the pathology of a variety of these ocular vascular disorders.

SUMMARY OF INVENTION

It is an object of the invention to provide methods for treating an ocular vascular disorder.

It is another object of the invention to provide method for inhibiting capillary permeability associated with macular edema in a mammal.

It is still another object of the invention to provide a method for inhibiting vascular endothelial growth factor (VEGF) induced neovascularization.

These and other objects of the invention are provided by one or more of the embodiments described below.

In one embodiment of the invention, there is provided a method for treating an ocular vascular disorder which comprises administrating to a mammal in need of such treatment a therapeutically effective amount of an inhibitor of the β isozyme of protein kinase C.

In another embodiment of the invention there is provided a method for treating macular degeneration in a mammal which comprises administrating to said mammal a therapeutically effective amount of an inhibitor of the β isozyme of protein kinase C.

In still another embodiment of the invention there is provided a method for inhibiting capillary permeability associated with macular edema in a mammal which comprises administrating to said mammal a capillary permeability inhibiting amount of an inhibitor of the β isozyme of protein kinase C.

In another embodiment of the invention there is provided a method for inhibiting vascular endothelial growth factor (VEGF) which comprises administering to said mammal a VEGF inhibiting amount of an inhibitor of the β isozyme of protein kinase C.

The present invention provides the art with the identity of compounds which are prophylactic and effective in treating a variety of ocular vascular disorders.

DETAILED DESCRIPTION OF THE INVENTION

Figure 1:
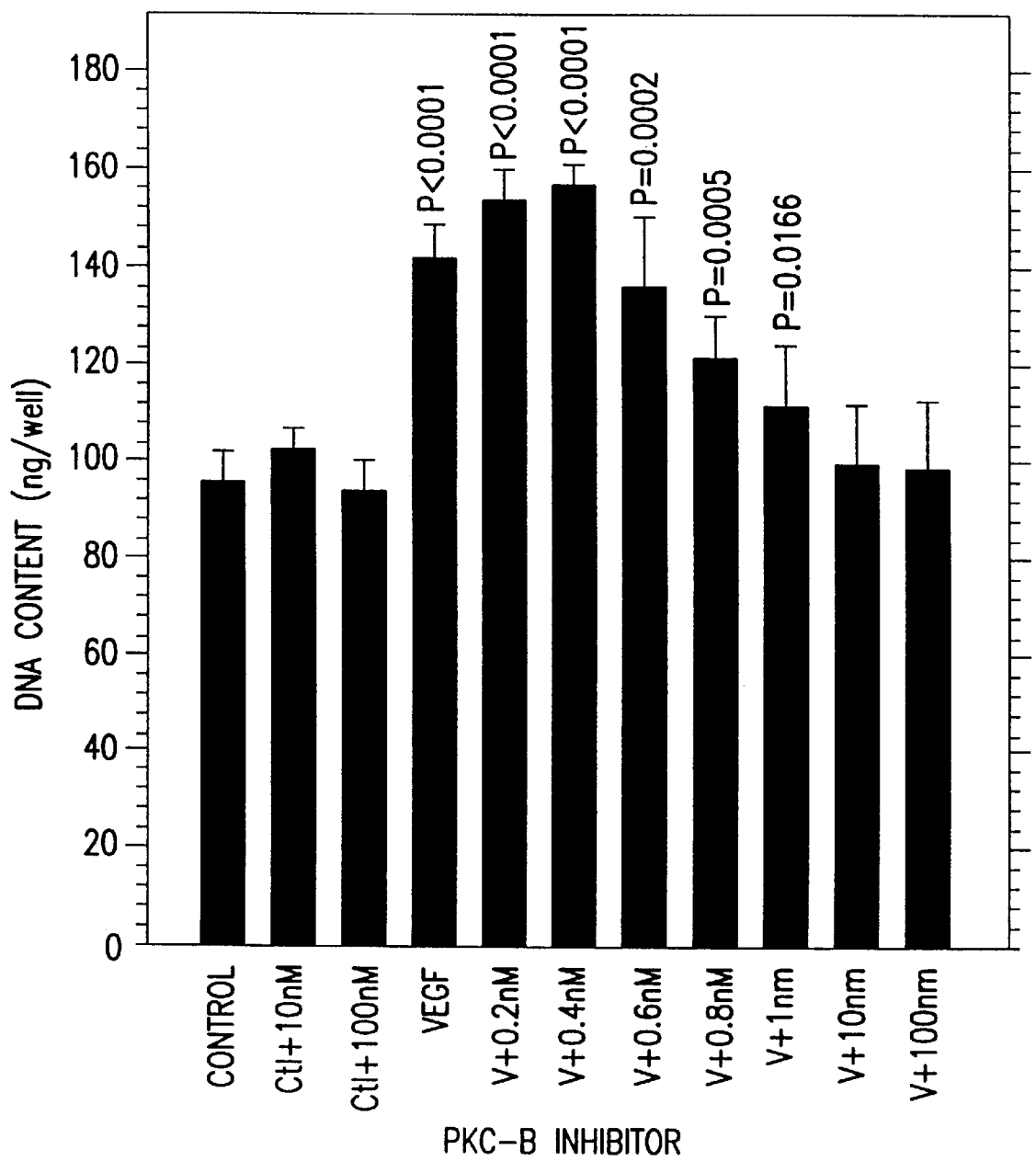
FIG. 1 shows the inhibitory effect of the PKC inhibitor, (S)-3,4-[N,N'-1,1'-((2"-ethoxy)-3'"(O)-4'"-(N,N-dimethylamino)-butane)-bis-(3,3'-indoly 1)]-1(H)-pyrrole-2,5-dione on recombinant human VEGF stimulated endothelial cell growth.

It is a discovery of the present invention that the therapeutic use of a particular class of protein kinase C inhibitors, i.e., inhibitors of the β isozyme of protein kinase C, and especially β isozyme selective inhibitors of PKC, counteracts the effects of VEGF. In particular, it is a discovery of the present invention that use of this particular class of protein kinase C inhibitors counteracts endothelial cell growth and capillary permeability, especially the endothelial cell growth and the capillary permeability stimulated by the growth factor VEGF. Consequently, such compounds can be used therapeutically to treat disorders associated with VEGF, in particular, a variety of ocular vascular disorders.

The method of this invention preferably utilizes those protein kinase C inhibitors that effectively inhibit the β isozyme. One suitable group of compounds are generally described in the prior art as bis-indolylmaleimides or macrocyclic bis-indolylmaleimides. Bis-indolylmaleimides well recognized in the prior art include those compounds described in U.S. Pat. No. 5,621,098, 5,552,396, 5,545,636, 5,481,003, 5,491,242, and 5,057,614, all incorporated by reference herein. Macrocyclic bis-indolylmaleimides are particularly represented by the compounds of formula I. These compounds, and methods for their preparation, have been disclosed in U.S. Pat. No. 5,552,396, which is incorporated herein by reference. These compounds are administered in a therapeutically effective amount to a mammal to inhibit endothelial cell growth or capillary permeability associated with VEGF and to inhibit VEGF effects associated with ocular disorders. These compounds can also be administered to patients at risk of the disease conditions mentioned above as prophylactics.

One preferred class of compounds for use in the method of the invention has the formula:

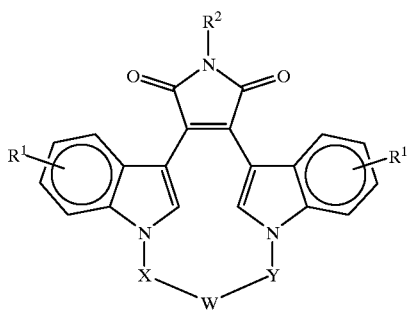

(I)

wherein:

W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R$^1$s are hydrogen or up to four optional substituents independently selected from halo, C$_1$C$_4$ alkyl, hydroxy, C$_1$–C$_4$ alkoxy, haloalkyl, nitro, NR$^4$R$^5$, or —NHCO (C$_1$–C$_4$ alkyl);

R$^2$ is hydrogen, CH$_3$CO—, NH$_2$, or hydroxy;

R$^3$ is hydrogen, (CH$_2$)$_m$aryl, C$_1$–C$_4$ alkyl, —COO(C$_1$–C$_4$ alkyl), —CONR$^4$R$^5$, —(C=NH)NH$_2$, —SO(C$_1$–C$_4$ alkyl), —SO$_2$ (NR$^4$R$^5$), or —SO$_2$ (C$_{1-C4}$ alkyl);

R$^4$ and R$^5$ are independently hydrogen, C$_1$–C$_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5, or a pharmaceutically acceptable salt, prodrug or ester thereof.

A more preferred class of compounds for use in this invention is represented by formula I wherein the moieties -X-W-Y- contain 4 to 8 atoms, which may be substituted or unsubstituted. Most preferably, the moieties -X-W-Y- contain 6 atoms.

Other preferred compounds for use in the method of this invention are those compounds of formula I wherein R$^1$ and R$^2$ are hydrogen; and W is a substituted alkylene, —O—, S—, —CONH—, —NHCO— or —NR$^3$—. Particularly preferred compounds for use in the invention are compounds of the formula Ia:

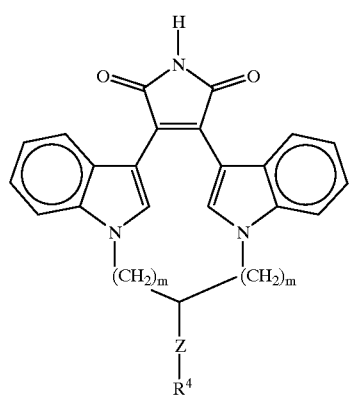

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$) (CF$_3$), —NH(CF$_3$), or —NR$^5$R$^6$; R$^5$ is hydrogen or C$_1$–C$_4$ alky; R$^6$ is hydrogen, C$_1$–C$_4$alkyl or benzyl; p is 0, 1, or 2; and m is independently 2 or 3, or a pharmaceutically acceptable salt, prodrug or ester thereof. Most preferred compounds of the formula Ia are those wherein Z is CH$_2$; and R$^4$ is —NH$_2$, —NH(CF$_3$), or —N(CH$_3$)$_2$, or a pharmaceutically acceptable salt, prodrug or ester thereof.

Other preferred compounds for use in the method of the present invention are compounds wherein W in formula I is —O—, Y is a substituted alkylene, and X is an alkylene. These preferred compounds are represented by formula Ib:

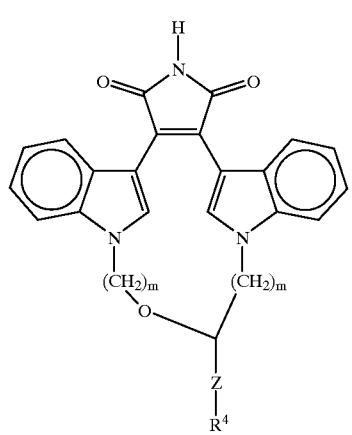

(Ib)

wherein Z is —(CH$_2$)$_p$—; R$^4$ is —NR$^5$R$^6$, —NH(CF$_3$), or —N(CH$_3$) (CF$_3$); R$^5$ and R$^6$are independently H or C$_1$–C$_4$ alkyl; p is 0, 1, or 2; and m is independently 2 or 3, or a pharmaceutically acceptable salt, prodrug or ester thereof. Most preferred compounds of formula Ib are those wherein p is 1; and R$^5$ and R$^6$ are methyl. Because they contain a basic moiety, the compounds of formulae I, Ia, and Ib can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and the like. Particularly the hydrochloric and mesylate salts are used.

In addition to pharmaceutically-acceptable salts, other salts also can exist. They may serve as intermediates in the purification of the compounds, in the preparation of other salts, or in the identification and characterization of the compounds or intermediates.

The pharmaceutically acceptable salts of compounds of formulae I, Ia, and Ib can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of formulae I, Ia, and Ib may exist; for example, W may contain a chiral carbon atom in the substituted alkylene moiety. The compounds are normally prepared as racemates and can conveniently be used as such. Alternatively, both individual enantiomers can be isolated or synthesized by conventional techniques if so desired. Such racemates and individual enantiomers and mixtures thereof form part of the compounds used in the methods of the present invention.

The compounds utilized in this invention also encompass the pharmaceutically acceptable prodrugs of the compounds of formulae I, Ia, and Ib. A prodrug is a drug which has been chemically modified and may be biologically inactive at its site of action, but which may be degraded or modified by one or more enzymatic or other in vivo processes to the parent bioactive form. This prodrug likely may have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H. Bundgaard, *Design of Prodrugs*, (1985). The synthesis of various bis-indole-N-maleimide derivatives is described in Davis et al. U.S. Pat. No. 5,057,614 and the synthesis of the preferred compounds suitable for use in this invention are described in the previously identified U.S. Pat. No. 5,552,396 and in Faul et al. EP publication 0 657 411 A1, all of which are incorporated herein by reference. One particularly preferred protein kinase -β inhibitor for use in the method of this invention is the compound described in Example 5g ((S)-3,4-[N,N'-1,1'-((2"-ethoxy)-3""(O)-4'"-(N,N-dimethylamino)-butane)-bis-(3,3'-indoly 1)]-1(H)-pyrrole-2,5-dione Hydrochloride Salt) of the aforementioned U.S. Pat. No. 5,552,396. This compound is a potent protein kinase C inhibitor. It is selective to protein kinase C over other kinases and is highly isozyme-selective, i.e., it is selective for the beta-1 and beta-2 isozymes. Other salts of this compound also would be favored, especially the mesylate salts.

A preferred mesylate salt can be prepared by reacting a compound of the formula II

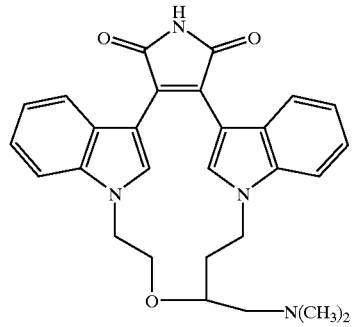

(II)

with methanesulfonic acid in a non-reactive organic solvent, preferably an organic/water mixture, and most preferably water-acetone. Other solvents such as methanol, acetone, ethylacetate and mixtures thereof are operable. The ratio of solvent to water is not critical and generally determined by the solubility of the reagents. Preferred solvent to water ratios are generally from 0.1:1 to 100:1 solvent to water by volume. Preferably, the ratio is 1:1 to 20:1 and most preferably 5:1 to 10:1. The optimal ratio is dependent on the solvent selected and is preferably acetone at a 9:1 solvent to water ratio.

The reaction usually involves approximately equimolar amounts of the two reagents, although other ratios, especially those wherein the methanesulfonic acid is in excess, are operative. The rate of addition of methanesulfonic acid is not critical to the reaction and may be added rapidly (<5 minutes) or slowly over 6 or more hours. The reaction is carried out at temperatures ranging from 0° C. to reflux. The reaction mixture is stirred until formation of the salt is complete, as determined by x-ray powder diffraction, and can take from 5 minutes to 12 hours.

The salts of the present invention are preferably and readily prepared as a crystalline, form. The trihydrate form of the salt may be readily converted to the monohydrate upon drying or exposure to 20–60% relative humidity. The salt is substantially crystalline demonstrating a defined melting point, birefringence, and an x-ray diffraction pattern. Generally, the crystals have less than 10% amorphous solid and preferably less than 5% and most preferably less than 1% amorphous solid.

The mesylate salt is isolated by filtration or other separation techniques appreciated in the art directly from the reaction mixture in yields ranging from 50% to 100%. Recrystallization and other purification techniques known in the art may be used to purify the salt further if desired.

Endothelial cells in tissue culture stimulated by growth factors such as VEGF exhibit a greater growth rate than the basal cellular growth rate. Experiments performed in the present invention have shown that when administered in vitro, at a concentration of about 0.1 to 100 nM, the protein kinase C inhibitor (S)-3,4-[N,N'-1,1'-((2"-ethoxy)-3'"(O)-4'"-(N,N-dimethylamino)-butane)-bis-(3,3 '-indoly 1)]-1 (H)-pyrrole-2,5-dione acid salt significantly inhibits growth factor (such as VEGF) stimulated non-basal cell growth.

Importantly, other testings have demonstrated that normal endothelial cell growth in tissue culture is not inhibited by this compound, as shown by the lack of inhibition of endothelial cell growth without VEGF stimulation in normoxic conditional media. In hypoxic conditioned media, the cell growth rate increases due to the increase in the endogenous growth factor, VEGF, content produced by the hypoxic cells. Again, the protein kinase C inhibitor (S)-3, 4-[N,N'-1,1'-((2"-ethoxy)-3'"(O)-4'"-(N,N-dimethylamino)-butane)-bis-(3,3'-indoly 1)]-1(H)-pyrrole-2,5-dione acid salt normalizes the cell growth induced by such hypoxic conditions.

Experiments provided in the present invention demonstrate that capillary permeability is also affected by growth factors such as VEGF. Testing has shown that in an animal model, VEGF significantly increases the capillary permeability up to 3 fold. This VEGF dependent capillary permeability increase is also dose dependent. According to the in vivo animal testing, administrating protein kinase C inhibitor at a concentration of about 25mg/kg/day prior to VEGF challenge greatly inhibited the capillary permeability induced by VEGF. Use of concentrations from 1 nM to 5 mM, and preferably from 1 nM to 500 nM are specifically contemplated. The inhibition can be up to 80% and is generally specific to growth factor induced capillary permeability. Capillary permeability can be measured by fluorescein angiography. Particularly in macular edema, fluorescein angiography is a retinal photographic procedure that involves injection of a fluoresecent dye into the bloodstream to detect areas of leakage in the retina.

Though not wishing to be limited to any technical explanation, applicants believe that alternations in retinal perfusion arising from decreased blood flow, retinal-capillary loss, peripheral-vasculature agenesis or obliteration, or separation of the choroidal blood supply from the retina all can result in relative retinal ischemia. This ischemia stimulates the synthesis and secretion of growth factors such as VEGF in retinal pericytes, endothelial cells, the retinal pigment epithelium, glial cells and possibly other cell types and subsequently leads to retinal neovascularization and increased capillary permeability. These conditions are associated with a variety of ocular vascular disorders. The inhibitors of the β isozyme of PKC described in the present invention can be used to treat the disease conditions associated with endothelial cell growth and capillary permeability, especially a variety of ocular vascular disorders.

Ocular vascular disorders treatable by the compounds of the present invention include but are not limited to macular degeneration, macular edema, vascular retinopathy, retinal vein occlusion, iris neovascularization, histoplasmosis, and ischemic retinal diseases. Macular degeneration may be age related. Macular edema can be associated with diabetes or central retinal occlusion. As used herein, the phrase vascular retinopathy does not include diabetic retinopathy but does include vascular retinopathy associated with sickle cell anemia, premature infants, and neovascularization of the angle or trabecular meshwork. Iris neovascularization can be diabetic or non-diabetic associated.

One skilled in the art will recognize that a therapeutically effective amount of an inhibitor of the β isozyme of protein kinase C in accordance with the present invention is the amount sufficient to inhibit the growth of endothelial cells or development of capillary permeability by inhibiting VEGF and that this amount varies, inter alia, depending upon an affected tissue size, the concentration of the compound in the therapeutic formulation, and the body weight of the patient. Generally, an amount of an inhibitor of the β isozyme of protein kinase C to be administered as a therapeutic agent for treating ocular vascular disorders will be determined on a case by case basis by the attending physician. As a guideline, the extent of the neovascularization, the body weight and age of the patient will be considered when setting an appropriate dose. Generally, a suitable dose is one that results is a concentration of the inhibitor of the β isozyme of protein kinase C at the treatment site in the range of 0.5 nM to 200 μM, and more usually 0.5 nM to 200 nM. It is expected that serum concentrations of 0.5 nM to 100 nM should be sufficient in most circumstances.

To obtain these treatment concentrations, a patient in need of treatment likely will be administered between about 0.001 mg per day per kg of body weight and 50.0 mg per day per kg. Usually, not more than about 1.0 to 10.0 mg per day per kg of body weight of the protein kinase C β inhibitor should be needed. As noted above, the above amounts may vary on a case-by-case basis.

The compounds of formula I and the preferred compounds of formula Ia and Ib are preferably formulated prior to administration. Suitable pharmaceutical formulations are prepared by known procedures using well known and readily available ingredients. In making the compositions suitable for use in the method of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application.

Some examples of suitable carriers, excipient, and diluents include lactose, dextrose, sucrose sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 0.05 mg to about 3 g, more usually about 750 mg of the active ingredient. However, it will be understood that the therapeutic dosage administered will be determined by the physician in the light of the relevant circumstances including the severity of the condition to be treated, the choice of compound to be administered and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, most of which may be administered orally, the compounds used in the method of the present invention also may be administered topically. Topical formulations include ointments, creams and gels.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate, hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compound) is added to the formulation at the desired concentration at a point preceding addition of the gelling agent.

The amount of compound incorporated into a topical formulation is not critical; the concentration should be within a range sufficient to permit ready application of the formulation to the affected tissue area in an amount which will deliver the desired amount of compound to the desired treatment site.

The customary amount of a topical formulation to be applied to an affected tissue will depend upon an affected tissue size and concentration of compound in the formulation. Generally, the formulation will be applied to the effected tissue in an amount affording from about 1 to about 500 $\mu$g compound per $cm^2$ of an affected tissue. Preferably, the applied amount of compound will range from about 30 to about 300 $\mu g/cm^2$, more preferably, from about 50 to about 200 $\mu g/cm^2$, and, most preferably, from about 60 to about 100 $\mu g/cm^2$.

The following formulation examples are illustrative only and are not intended to limit the scope of the invention in any way.

Formulation 1
Hard gelatin capsules are prepared using the following ingredients

|  | Quantity (mg/capsule) |
| --- | --- |
| Active agent | 250 |
| starch, dried | 200 |
| magnesium stearate | 10 |
| Total | 460 mg |

The above ingredients are mixed and filled into hard gelatin capsules in 460 mg quantities.

Formulation 2
A tablet is prepared using the ingredients below

|  | Quantity (mg/capsule) |
| --- | --- |
| Active agent | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3
Tablets each containing 60 mg of active ingredient are made as follows

|  | Quantity (mg/tablet) |
| --- | --- |
| Active agent | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLES

These examples all demonstrate the use of (S)-3,4-[N,N'-1,1'-((2"-ethoxy)-3'"(O)-4'"-(N,N-dimethylamino)-butane)-bis-(3,3'-indolyl )]-1(H)-pyrrole-2,5-dione hydrochloride salt to inhibit in vitro endothelial cell growth and to inhibit in vivo increased capillary permeability stimulated by VEGF.

Example 1

In this example, the inhibitory effect of the noted compound on VEGF stimulated endothelial cell growth was examined using recombinant human VEGF.

Bovine retinal endothelial cells were isolated from fresh calf eyes by homogenization and a series of filtration steps. Primary endothelial cell cultures were grown in fibronectin (NYBen Reagents, New York Blood Center)-coated dishes (Costar) containing Dulbecco's modified Eagle's medium (DMEM) with 5.5 mM glucose, 10% plasma-derived horse serum (Wheaton Scientific). 50 mg of heparin per liter and 50 units of endothelial cell growth factor per liter (Boehringer Mannheim). After the cells reached confluence, the medium was changed to include 5% fetal bovine serum (HyClone). Medium was changed every 3 days. Endothelial cell homogeneity was confirmed with anti-factor VIII antibodies.

The effect of the noted PKC inhibitor on VEGF action in vitro was evaluated by using sparsely plated cultures of the bovine retinal microvascular endothelial cells, which undergo growth stimulation upon addition of VEGF. Bovine retinal endothelial cells were plated sparsely (~2500 cells per well) in 24-well dishes (Costar) and incubated overnight in DMEM containing 10% calf serum (GIBCO). The medium was changed the next day.

To examine the impact of the noted PKC inhibitor on endothelial cell growth, one set of experiments was conducted in which the cell growth in the absence of any active agent served as a control, and then the impact of the addition of the noted PKC inhibitor in both the presence of VEGF (25 ng/ml; Genentech) and in the absence of VEGF was examined. After incubation at 37° C. for 4 days, the cells were lysed in 0.1% sodium dodecyl sulfate (SDS) and DNA content was measured using Hoechst 33258 dye and a fluorometer (model TKO-100; Hoefer).

All determinations were performed at least in triplicate and experiments were repeated a minimum of three times. Results are expressed as means ±SD for all experiments. Analysis of in vitro results was performed by non-paired Student's t test.

A P value of <0.050 was considered statistically significant.

FIG. 1 illustrates the results obtained using recombinant VEGF. As shown by the three left-most columns of the figure, the addition of the noted PKC inhibitor to the endothelial cell culture had essentially no impact on the basal growth rate (column one). The growth rate increased substantially upon the addition of VEGF (fourth column). This growth rate was curtailed significantly upon the addition of >0.5 nM of the noted PKC inhibitor (four right-most columns).

Example 2

This example is similar to the work reported in FIG. 1 and further illustrates the inhibitory effect of the noted PKC inhibitor on VEGF stimulated endothelial cell growth using recombinant human VEGF.

Using the procedures of Example 1, bovine retinal endothelial cells were isolated and grown; then sparsely plated cultures were prepared. Again, using the procedure of Example 1, experiments were conducted in which the affect of the noted PKC inhibitor on endothelial cell growth in both the presence of VEGF (25 ng/ml; Genentech) and in the absence of VEGF was examined. After incubation at 37° C. for 4 days, the cells were lysed in 0.1% sodium dodecyl sulfate (SDS) and DNA content was measured using Hoechst 33258 dye and a fluorometer (model TKO-100; Hoefer).

Figure 2:
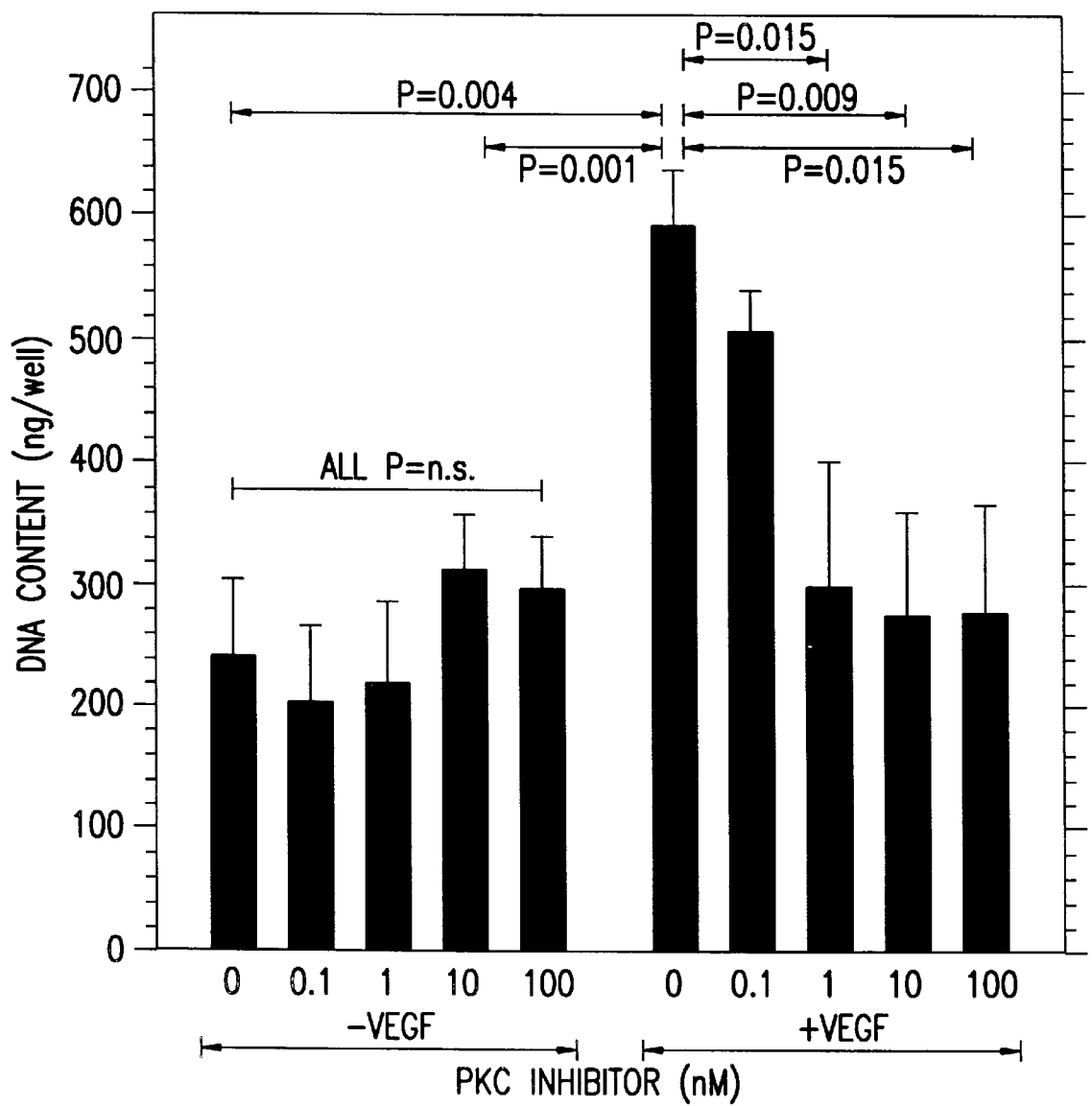
FIG. 2 further illustrates the inhibitory effect of the PKC inhibitor, (S)-3,4-[N,N'-1,1'-((2"-ethoxy)-3'"(O)-4'"-(N,N-dimethylamino)-butane)-bis-(3,3'-indoly 1)]-1(H)-pyrrole-2,5-dione on recombinant human VEGF stimulated endothelial cell growth.

FIG. 2 illustrates the results of this work. As shown by the columns above the legend –VEGF, the addition of the noted PKC inhibitor to the endothelial cell culture at from 0.1 nM to 100 nM had essentially no impact on the basal growth rate of the cells. Stimulation of the endothelial cells with recombinant human VEGF (25 ng/ml) produced a significant increase in cellular DNA content after 4 days, indicative of an increase in growth rate, compared with unstimulated cells (compare –VEGF at 0 with +VEGF at 0). This growth rate was curtailed significantly upon the addition of the noted PKC inhibitor (four right-most columns above legend +VEGF). In particular, the VEGF stimulatory capacity was reduced slightly in the presence of 0.1 nM of the PKC inhibitor and was essentially entirely eliminated by simultaneous addition of 1 nM and greater of the PKC inhibitor.

Example 3

This example examines the impact of the noted PKC inhibitor on the activity of endogenous VEGF expressed upon culturing retinal pericytes under hypoxic conditions.

Bovine retinal endothelial cells and retinal pericytes were isolated from fresh calf eyes by homogenization and a series of filtration steps. The endothelial cells were grown and sparsely cultured on plates using the procedures of Example 1. Using similar techniques, bovine retinal pericytes were cultured in DMEM/5.5 mM glucose with 20% fetal bovine serum.

Hypoxic conditioned medium for endogenous VEGF expression and normoxic conditioned control medium were prepared respectively according to the following procedures. Confluent retinal pericyte monolayers were exposed for 24 hr to 2% $O_2$/5% $CO_2$/93% $N_2$ using a Lab-Line Instruments advanced computer controlled infrared water-jacketed $CO_2$ incubator with reduced oxygen control (model 480). All cells were maintained at 37° C. and showed no morphologic changes by light microscopy, excluded trypan blue dye (>98%) and could subsequently be passaged normally. Cells incubated under normoxic conditions (95% air/5% $CO_2$) from the same batch and passage were used as controls. Medium was subsequently collected and filtered (Nalgene; 0.22 $\mu$m) prior to use.

In this example, experiments were conducted in which the affect of the noted PKC inhibitor on endothelial cell growth in the presence of either normoxic conditioned media or hypoxic conditioned media was examined. As was done in the previous examples, after incubation at 37° C. for 4 days, the cells were lysed in 0.1% sodium dodecyl sulfate (SDS) and DNA content was measured using Hoechst 33258 dye and a fluorometer (model TKO-100; Hoefer).

Figure 3:
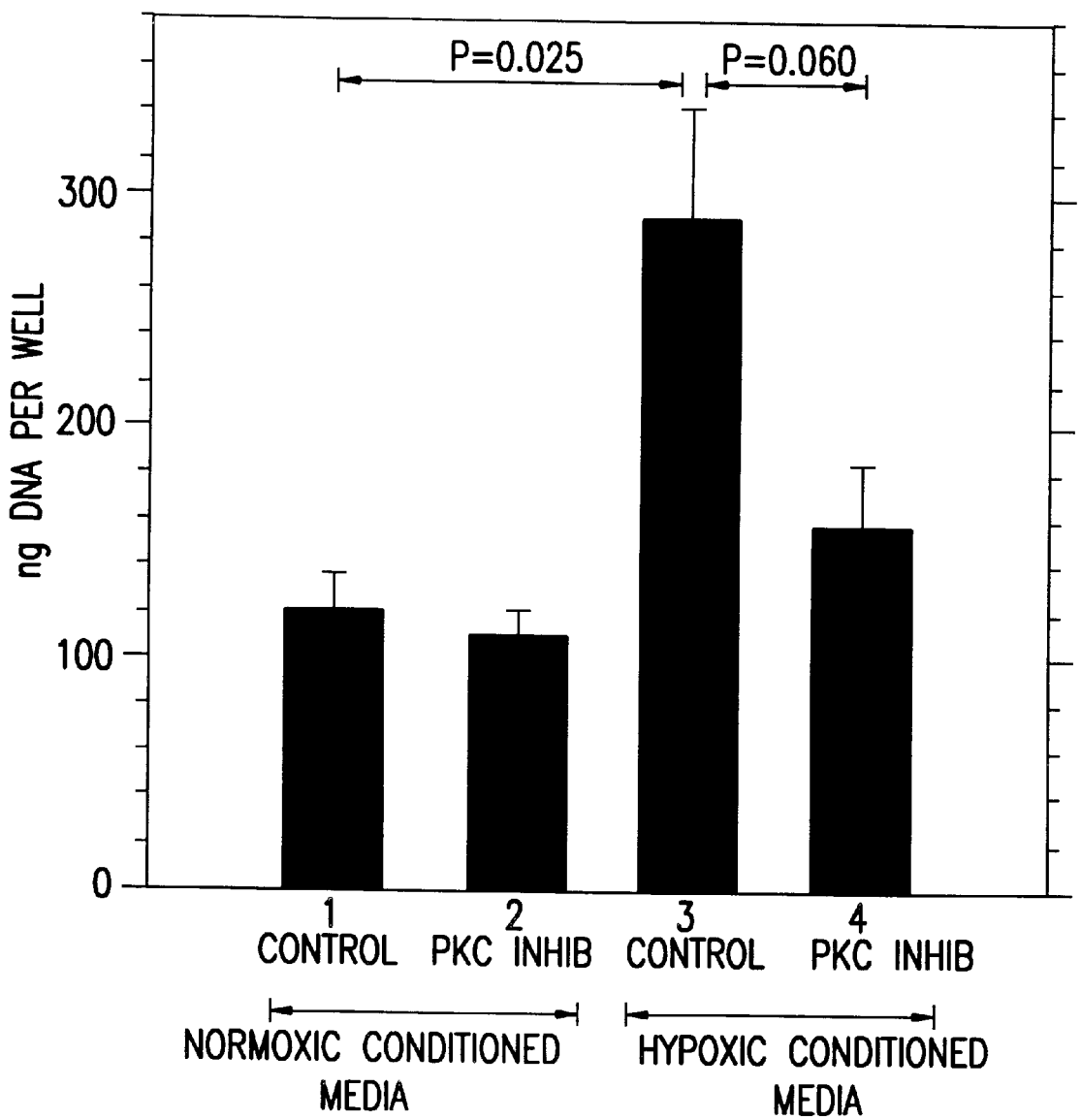
FIG. 3 shows the impact of the PKC inhibitor on the activity of endogenous VEGF expressed upon culturing retinal pericytes under hypoxic conditions.

In the tests reported in FIG. 3, the noted PKC inhibitor was used at a concentration of 10 nM. As shown in FIG. 3, retinal endothelial cell growth was stimulated by conditioned medium from retinal pericytes cultured under hypoxic conditions known to induce VEGF expression (compare column 1 to column 3 in FIG. 3). This growth stimulation was suppressed (normalized) in the presence of the hydrochloric acid salt of (S)-3,4-[N,N'-1,1-((2"-ethoxy)-3'"(O)-4'"-(N,N-dimethylamino)-butane)-bis-(3,3'-indolyl)]-1(H)-pyrrole-2,5-dione of the PKC inhibitor (compare 3 to column 4).

Example 4

This example is similar to the work reported in FIGS. 1 and 2 and further illustrates the inhibitory effect of the noted PKC inhibitor on VEGF stimulated endothelial cell growth using recombinant human VEGF.

Using the procedures of Example 1, bovine retinal endothelial cells were isolated and grown; then sparsely plated cultures were prepared. Again, using the procedure of Example 1, experiments were conducted in which the affect of the noted PKC inhibitor on endothelial cell growth in both the presence (+VEGF)(25 ng/ml; Genentech) and absence of VEGF (–VEGF) were examined. As above, after incubation at 37° C. for 4 days, the cells were lysed in 0.1% sodium dodecyl sulfate (SDS) and DNA content was measured using Hoechst 33258 dye and a fluorometer (model TKO-100; Hoefer).

Figure 4:
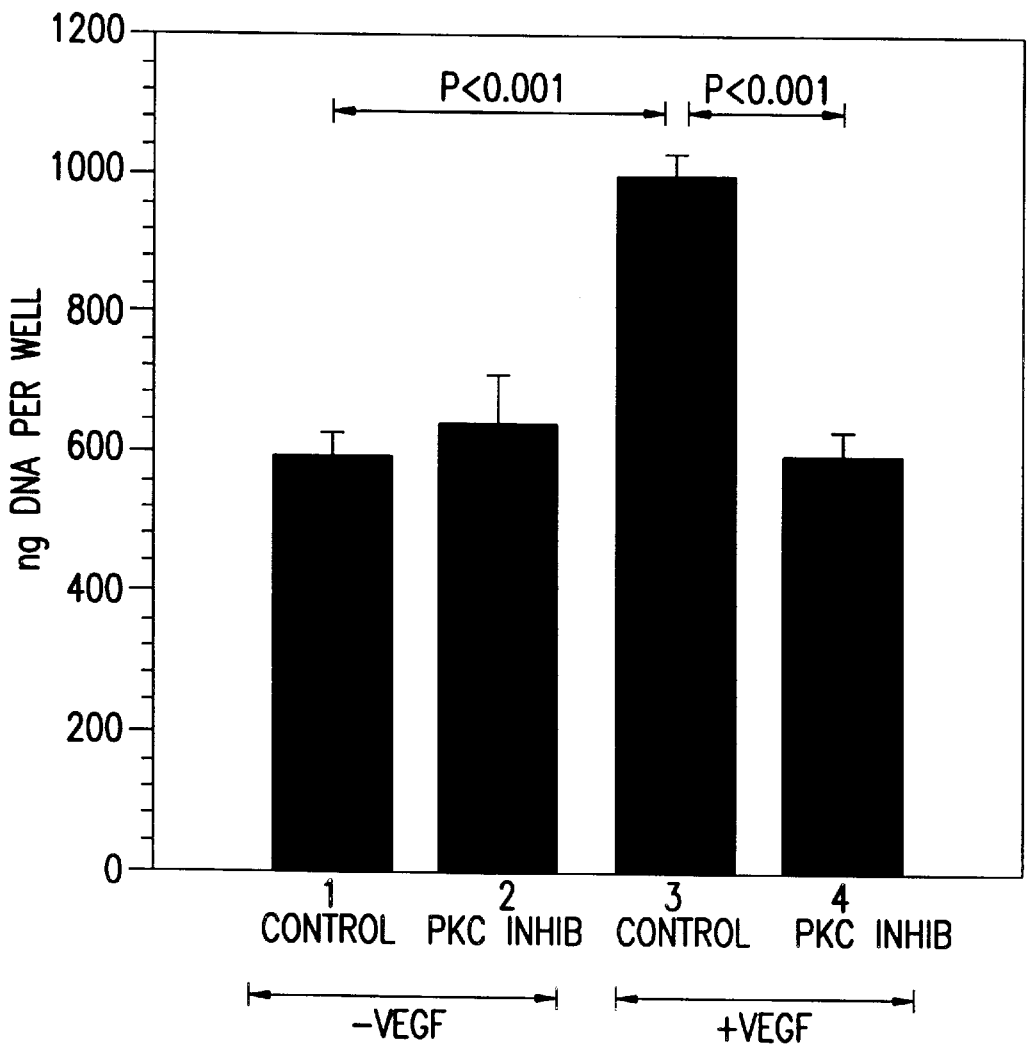
FIG. 4 further illustrate the inhibitory effect of the PKC inhibitor on recombinant human VEGF stimulated endothelial cell growth.

FIG. 4 illustrates the results of this work. As shown by the columns above the legend −VEGF, the addition of the noted PKC inhibitor to the endothelial cell culture at a concentration of 10 nM had essentially no impact on the basal growth rate of the cells. Stimulation of the endothelial cells with recombinant human VEGF (25 ng/ml) produced a significant increase in cellular DNA content, indicative of an increase in growth rate, compared with unstimulated cells (compare −VEGF Control with +VEGF Control). This growth rate was curtailed significantly upon the addition of the noted PKC inhibitor at a concentration of 10 nM.

These results demonstrate that the disclosed class of PKC inhibitors and particularly, (S)-3,4-[N,N'-1,1'-((2'-ethoxy)-3'''(O)-4'''-(N,N-dimethylamino)-butane)-bis-(3,3'-indolyl)]-l(H)-pyrrole-2,5-dione, prevents in vitro stimulation of retinal endothelial cell growth by both exogenous and hypoxia-induced VEGF. Since VEGF expression has been linked closely with neovascularization associated with macular degeneration, these results support the use of these PKC inhibitors as a therapy for the treatment of macular degeneration.

Example 5

This example demonstrates the time course of VEGF induced retinal permeability.

One eye of each rat received an intervitreal injection of 2.0 ng of VEGF (estimated final concentration 25 ng/ml). The contra-lateral eye received a similar volume of control solution. After 10 minutes, 30 microliters of fluorescein was injected through the catheter into the right jugular vein. Fluorphotometry of the vitreous was performed at the indicated times after fluorescein injection.

Figure 5A:
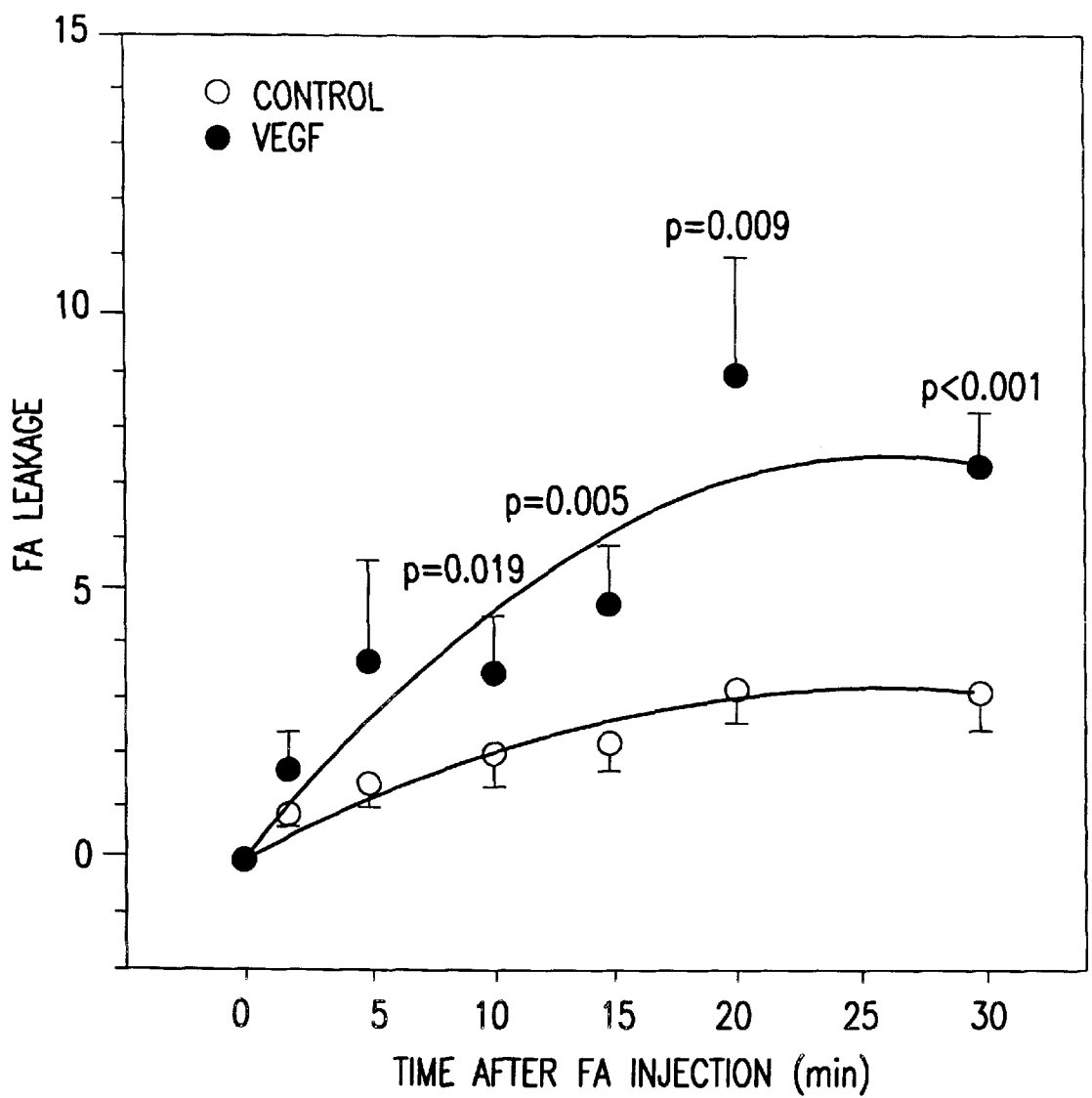
FIGS. 5A, 5B show the time course of VEGF induced retinal permeability.
Figure 5B:
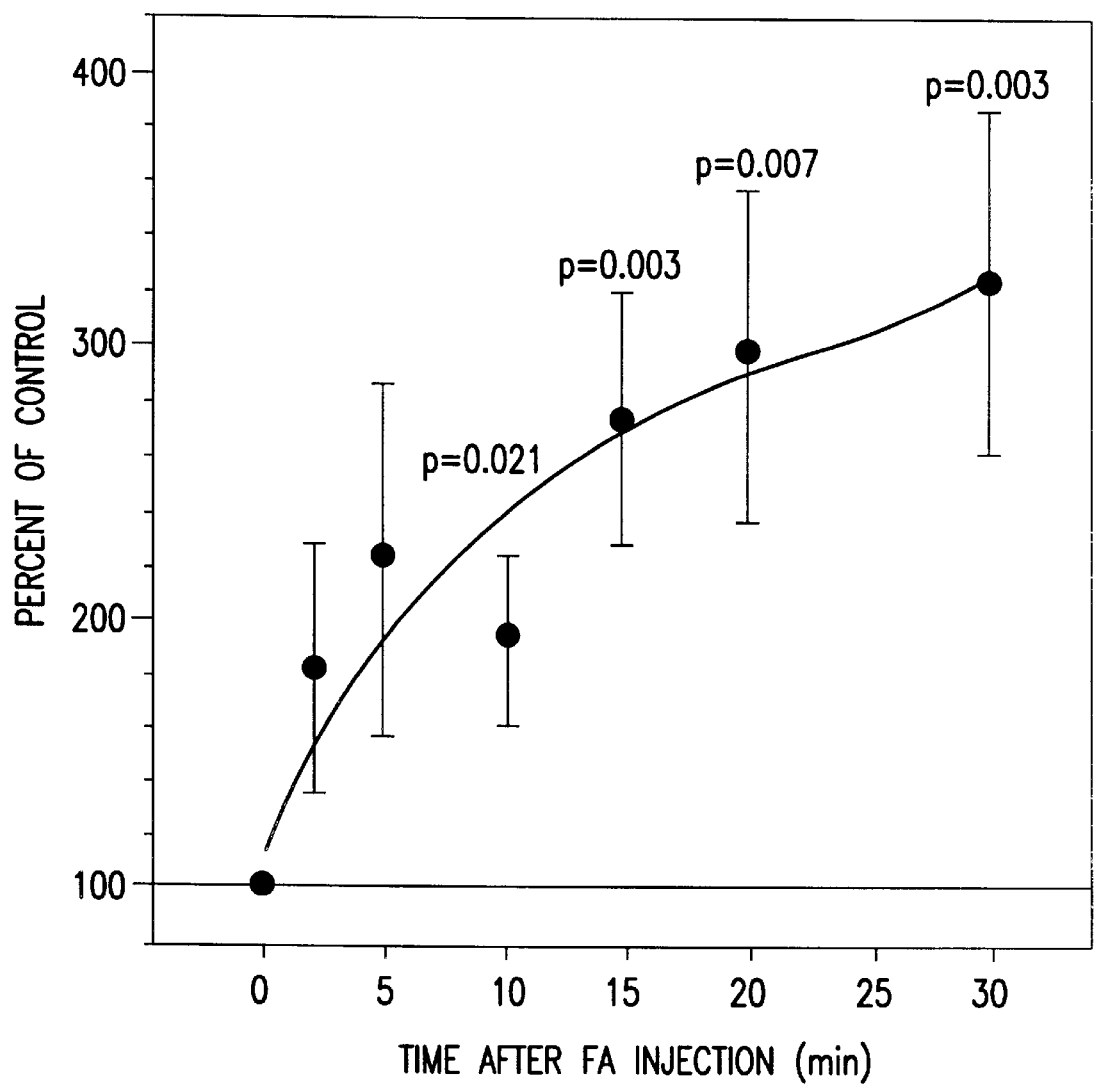

As shown in FIG. 5A, there is a clear increase in permeability of fluorescein into the vitreous in the eyes treated with VEGF. This becomes statistically significant within 10 minutes of fluorescein angiogram injection and is maintained for at least 30 minutes. FIG. 5B shows that this stimulation expressed as percent of control demonstrating that there is additional fluorescein leakage on the VEGF treated eyes over time.

Example 6

This example shows the dose response of retinal permeability to fluorescein in response to VEGF.

Figure 6:
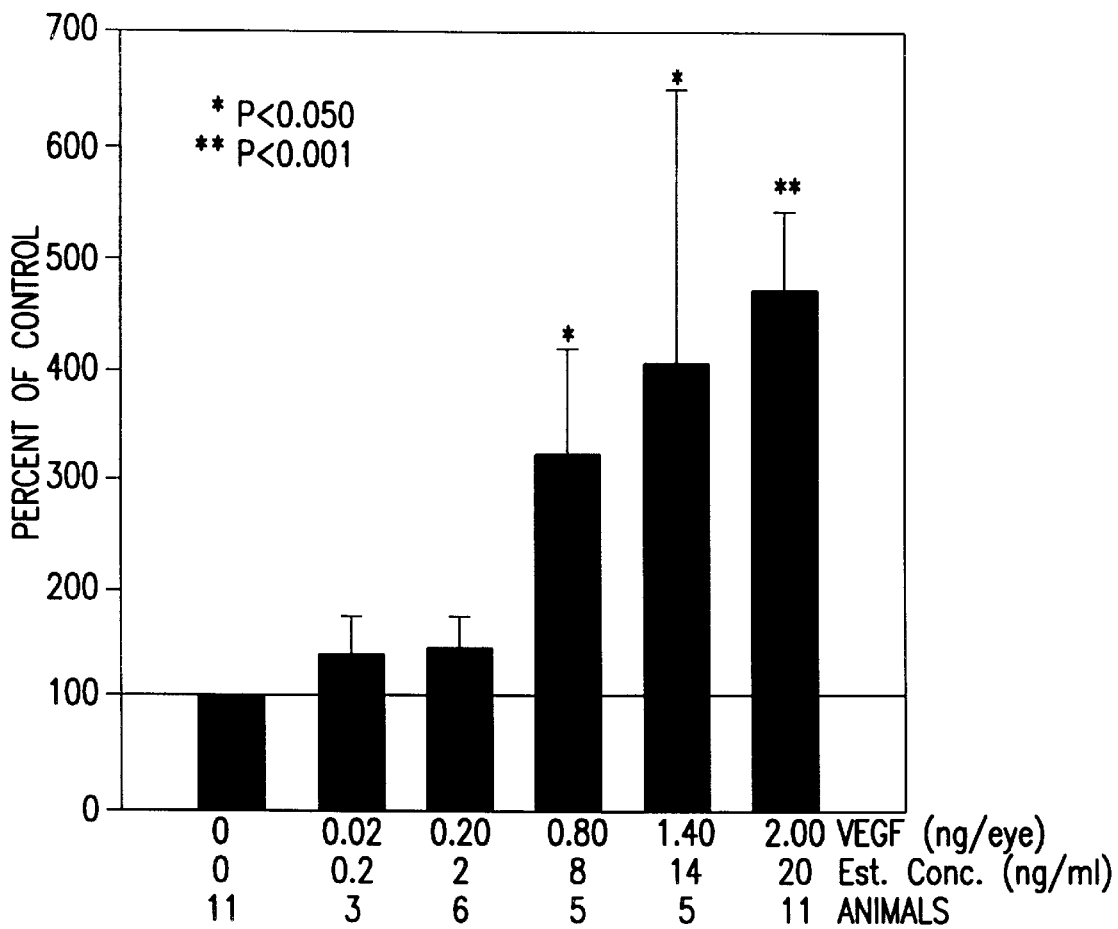
FIG. 6 demonstrates the response of fluorescein retinal permeability to VEGF.

One eye of each animal was injected with control while the contra-lateral eye was injected with various doses of VEGF. 10 minutes later intravenous fluorescein was injected and the amount of vitreous leakage analyzed after 30 minutes. As shown in FIG. 6, there was a VEGF dose dependent increase of retinal permeability.

Stimulation was maxima by 14 to 20 ng/ml which is known to be obtained in humans.

Example 7

This example demonstrates that the effect of intravitreal PKC inhibitor (S)-3,4-[N,N'-1,1'-((2"-ethoxy)-3'''(O)-4'''-(N,N-dimethylamino)-butane)-bis-(3,3'-indoly 1)]-1(H)-pyrrole-2,5-dione hydrochloride salt and its stimulation on retinal permeability.

Figure 7:
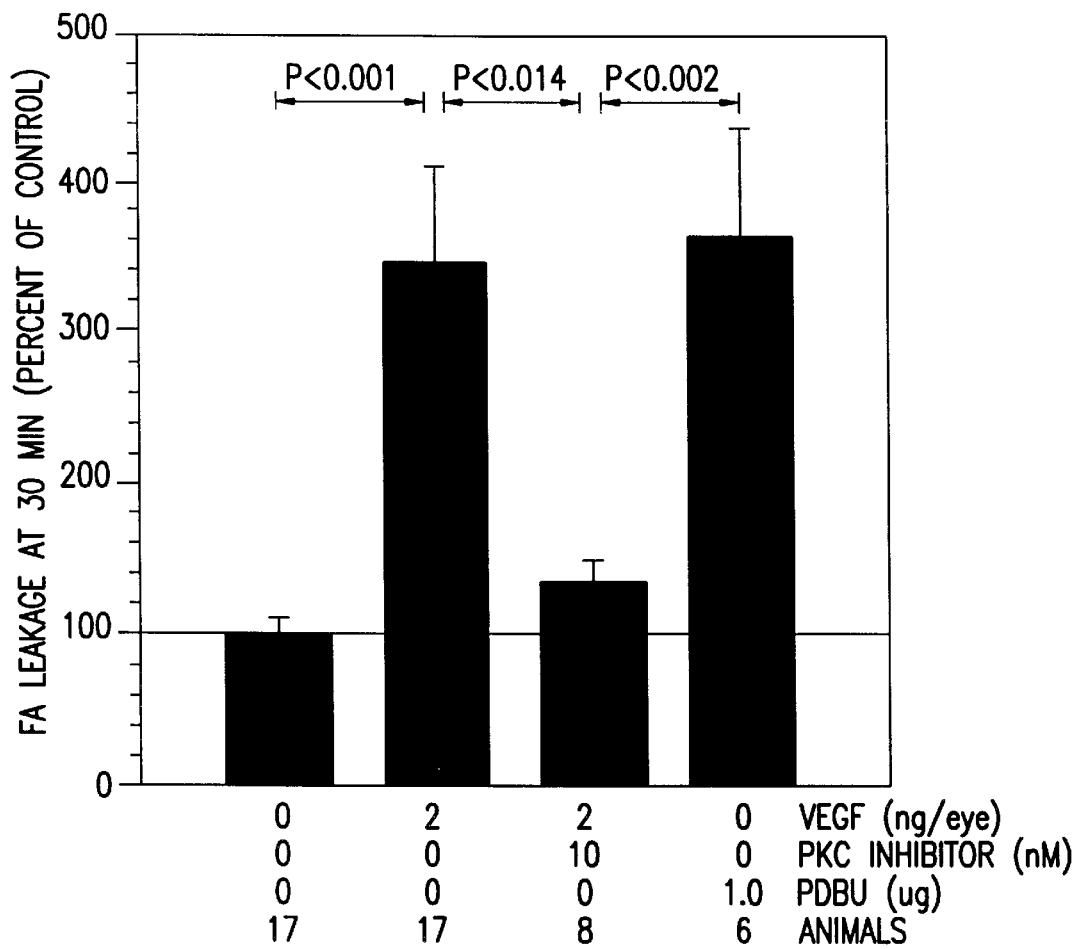
FIG. 7 demonstrates the effect of intravitreal PKC inhibition and stimulation on retinal permeability.

Eyes of rats were either injected with 2.0 ng VEGF per eye, 10 nM of the PKC βinhibitor, or one microgram of PDBU (a PKC agonist) as indicated in FIG. 7. PKCβ inhibitor was injected 15 minutes prior to VEGF addition. 10 minutes after VEGF addition, intravenous fluorescein was given and fluorescein in the vitreous was assessed after 30 minutes.

As shown in FIG. 7, intravitreal injection of VEGF showed the expected stimulation of retinal permeability. Intravitreal injection of PKC β inhibitor 15 minutes prior to injection of VEGF eliminated the majority of the permeability response. Direct stimulation of protein kinase C by injection of PDBU demonstrated an increase in permeability very similar to VEGF.

Example 8

This example demonstrates the inhibition of retinal permeability in response to VEGF by the orally administered protein kinase C β inhibitor (S)-3,4-[N,N'-1,1'-((2"-ethoxy)-3'''(O)-4'''-(N,N-dimethylamino)-butane)-bis-(3,3'-indoly 1)]-1(H)-pyrrole-2,5-dione hydrochloride salt.

Figure 8A:
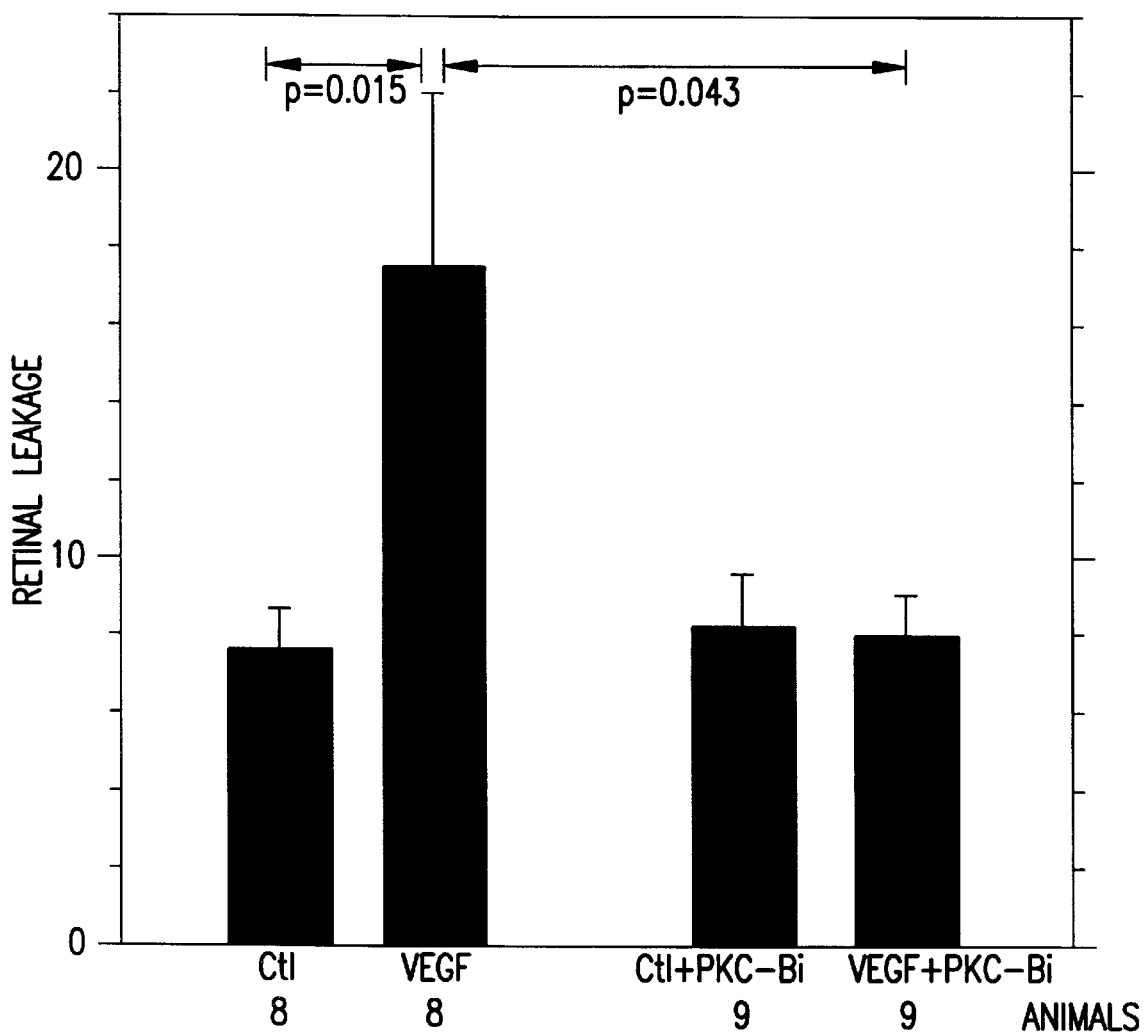
FIGS. 8A, 8B show the inhibition of retinal permeability in response to VEGF by orally administered protein kinase C β inhibitor.
Figure 8B:
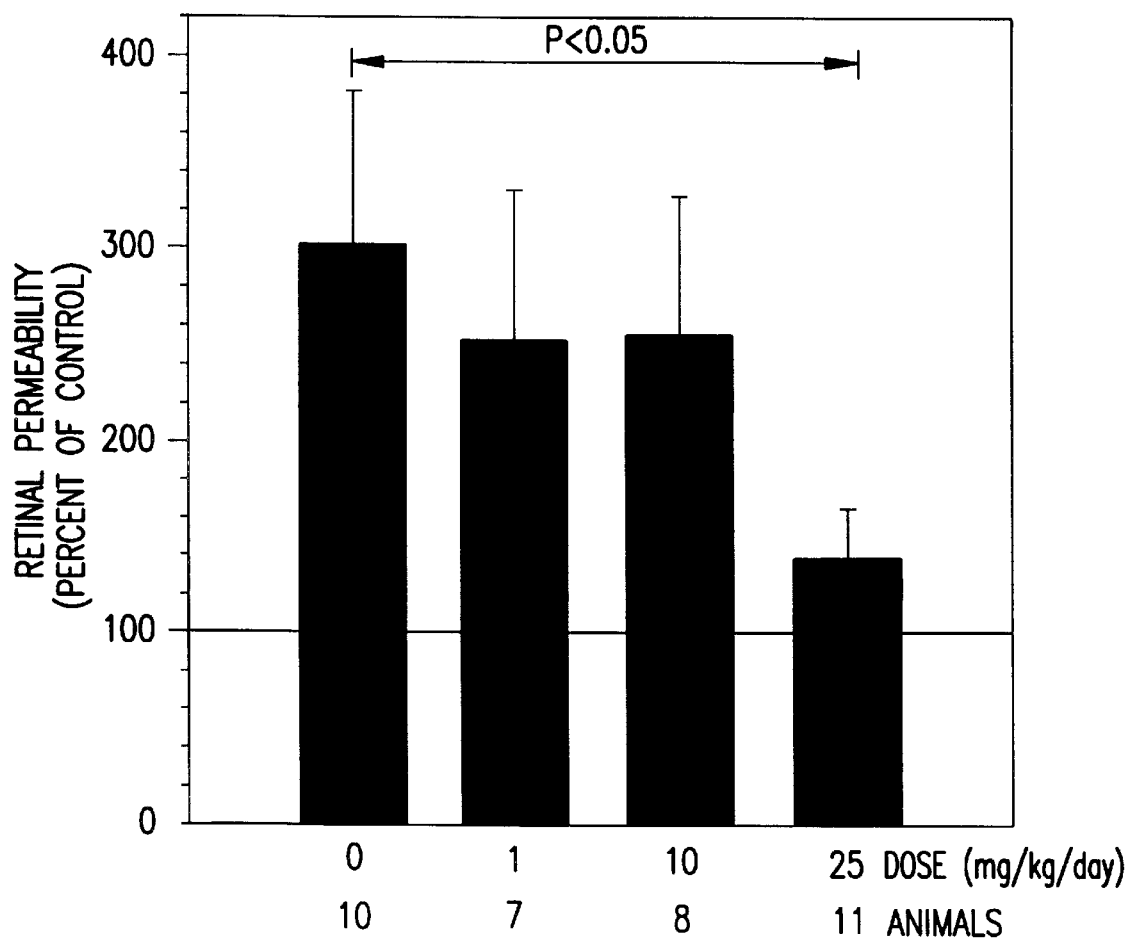

Rats were fed chow mixed with protein kinase C β inhibitor at the doses indicated in FIGS. 8A and 8B. After one week on this chow, retinal permeability in response to 2.0 ng of intravitreally injected VEGF was determined as discussed previously. Oral administration of the PKCβ inhibitor of this invention for one week reduced the retinal permeability in response to VEGF. This was most notable at higher doses.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

What is claimed is:

1. A method for treating an ocular vascular disorder, wherein the ocular vascular disorder is not diabetic retinopathy and wherein the ocular vascular disorder is VEGF-related, which comprises administering to a mammal in need for such treatment, a therapeutically effective amount of an inhibitor which is selective for a β isozyme of protein kinase C.

2. The method of claim 1 wherein the inhibitor which is selective for the β isozyme of protein kinase C is a bis-indolylmaleimide or a macrocyclic bis-indolylmaleimide.

3. The method of claim 1 wherein the β isozyme for which the inhibitor is selective is selected from the group consisting of beta-1 and beta-2 isozymes.

4. The method of claim 3 wherein the protein kinase C inhibitor has the following formula:

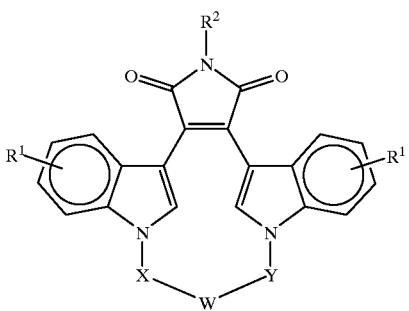

(I)

wherein:

W is —O—, —S—, —SO—, —SO$_2$—, —CO—, $C_2$–$C_6$ alkylene, substituted alkylene, $C_2$–$C_6$ alkenylene, -aryl-, -aryl($CH_2$)$_m$O—, -heterocycle-, -heterocycle-($CH_2$)$_m$O—, -fused bicyclic-, -fused bicyclic-($CH_2$)$_m$O—, —NR$^3$—, —NOR$^3$—, —CONH—, or —NHCO—;

X and Y are independently $C_1$–$C_4$ alkylene, substituted alkylene, or together X, Y, and W combine to form —(CH$_2$)$_n$—AA—;

R$^1$s are hydrogen or up to four optional substituents independently selected from halo, $C_1$–$C_4$ alkyl, hydroxy, $C_1$–$C_4$ alkoxy, haloalkyl, nitro, NR$^4$R$^5$, or —NHCO($C_1$–$C_4$ alkyl);

R$^2$ is hydrogen, CH$_3$CO—, NH$_2$, or hydroxy;

R$^3$ is hydrogen, (CH$_2$)$_m$aryl, $C_1$–$C_4$ alkyl, —COO($C_1$–$C_4$ alkyl), —CONR$^4$R$^5$, —(C=NH)NH$_2$, —SO($C_1$–$C_4$ alkyl), —SO$_2$ (NR$^4$R$^5$), or —SO$_2$ ($C_{1-C4}$ alkyl);

R$^4$ and R$^5$ are independently hydrogen, $C_1$–$C_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5, or a pharmaceutically acceptable salt, prodrug or ester thereof.

5. The method of claim 4 wherein the protein kinase C inhibitor has the following formula:

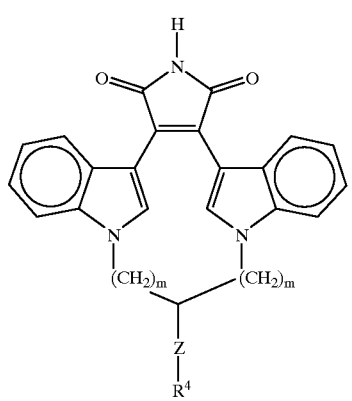

(Ia)

wherein Z is —(CH$_2$)$_p$— or —(CH$_2$)$_p$—O—(CH$_2$)$_p$—; R$^4$ is hydroxy, —SH, $C_1$–$C_4$ alkyl, (CH$_2$)$_m$aryl, —NH(aryl), —N(CH$_3$) (CF$_3$), —NH(CF$_3$), or —NR$^5$R$^6$; R$^5$ is hydrogen or $C_1$–$C_4$ alky; R$^6$ is hydrogen, $C_1$–$C_4$alkyl or benzyl; p is 0, 1, or 2; and m is independently 2 or 3, or a pharmaceutically acceptable salt, prodrug or ester thereof.

6. The method of claim 4 wherein the protein kinase C inhibitor has the following formula:

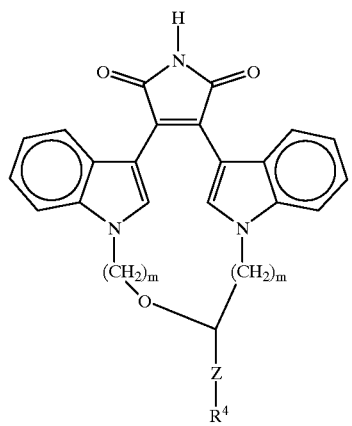

(Ib)

wherein Z is —(CH$_2$)$_p$—; R$^4$ is —NR$^5$R$^6$, —NH(CF$_3$), or —N(CH$_3$) (CF$_3$); R$^5$ and R$^6$ are independently H or $C_1$–$C_4$ alkyl; p is 0, 1, or 2; and m is independently 2 or 3, or a pharmaceutically acceptable salt, prodrug or ester thereof.

7. The method of claim 4, wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or its pharmaceutically acceptable acid salt.

8. The method of claim 1 wherein the VEGF-related ocular vascular disorder is selected from the group consisting of macular degeneration, macular edema, vascular retinopathy, iris neovascularization, retinal vein occlusion, histoplasmosis, and ischemic retinal disease.

9. The method of claim 1 wherein the VEGF-related ocular vascular disorder is selected from the group consisting of macular degeneration, macular edema, and retinal vein occlusion.

10. The method of claim 8 wherein said vascular retinopathy is retinopathy of prematurity.

11. A method for inhibiting endothelial cell growth stimulated by VEGF, which comprises administering to a mammal in need of such treatment a therapeutically effective amount of an inhibitor which is selective for a β isozyme of protein kinase C.

12. A method for inhibiting VEGF stimulated capillary permeability associated with edema, which comprises administering to a mammal in need of such treatment a therapeutically effective amount of an inhibitor which is selective for a β isozyme of protein kinase C.

* * * * *